(12) United States Patent
Caderas

(10) Patent No.: US 7,272,983 B2
(45) Date of Patent: Sep. 25, 2007

(54) PROBE-HOLDER ARMATURE WITH A SENSOR PROBE

(75) Inventor: Daniel Caderas, Lohn (CH)

(73) Assignee: Mettler-Toledo AG, Greifensee (CH)

( * ) Notice: Subject to any disclaimer, the term of this patent is extended or adjusted under 35 U.S.C. 154(b) by 304 days.

(21) Appl. No.: 11/075,483

(22) Filed: Mar. 9, 2005

(65) Prior Publication Data
US 2005/0229727 A1   Oct. 20, 2005

Related U.S. Application Data

(63) Continuation of application No. PCT/EP03/50604, filed on Sep. 1, 2003.

(30) Foreign Application Priority Data
Sep. 9, 2002  (DE) ............... 102 41 833

(51) Int. Cl.
*G01D 21/00* (2006.01)
(52) U.S. Cl. .................................. 73/866.5
(58) Field of Classification Search ............... 73/866.5, 73/863.82, 863.85, 86; 374/148, 208
See application file for complete search history.

(56) References Cited

U.S. PATENT DOCUMENTS

| 5,011,587 | A | 4/1991 | Schmidt |
| 5,296,197 | A * | 3/1994 | Newberg et al. ............ 422/103 |
| 6,640,658 | B1 * | 11/2003 | Guerrero et al. ........... 73/866.5 |
| 6,773,678 | B2 | 8/2004 | Cummings et al. |
| 6,860,162 | B1 * | 3/2005 | Jaeger ..................... 73/863.85 |

FOREIGN PATENT DOCUMENTS

| DE | 37 09 019 A1 | 9/1988 |
| DE | 39 40 948 A1 | 6/1991 |
| DE | G 92 02 350.9 | 4/1992 |
| DE | 197 20 504 A1 | 5/1997 |
| DE | 195 46 266 C2 | 6/1997 |
| DE | 197 23 681 C2 | 12/1998 |
| DE | 198 43 553 A1 | 4/2000 |
| DE | 100 24 564 A1 | 11/2001 |
| EP | 0 372 121 B1 | 6/1990 |
| EP | 0 414 032 A1 | 2/1991 |
| EP | 0 545 177 A1 | 6/1993 |
| EP | 0 590 290 A1 | 4/1994 |
| EP | 0 882 896 A1 | 12/1998 |
| EP | 000882896 A1 * | 12/1998 |
| WO | WO83/03778 * | 11/1983 |
| WO | WO 83/03778 | 11/1983 |

* cited by examiner

*Primary Examiner*—Robert Raevis
(74) *Attorney, Agent, or Firm*—Standley Law Group LLP

(57) ABSTRACT

A probe-holder armature contains a sensor probe that is removably arranged in the forward portion of an immersion tube which is axially movable in a housing between a retracted rest position and a deployed working position. The sensor probe in its installed condition forms a medium-tight closure of the immersion tube. The immersion tube contains a removable insert which can be held in a fixed position by means of a closure member. By means of the insert, the sensor probe in its installed position is pushed forward against a forward stop of the immersion tube. A safety device prevents an axial movement of the immersion tube out of its rest position if one or more of the three components sensor probe, insert and closure member are missing.

11 Claims, 3 Drawing Sheets

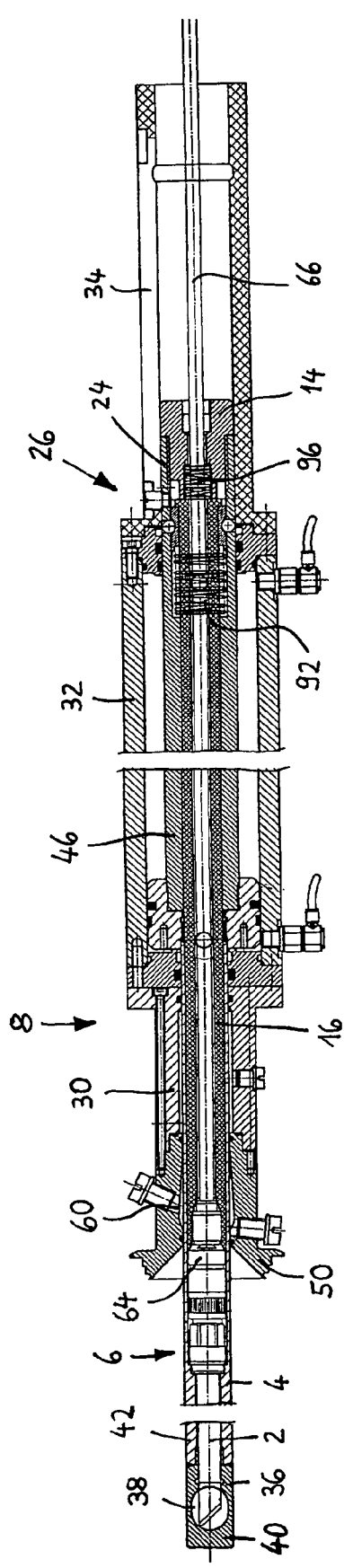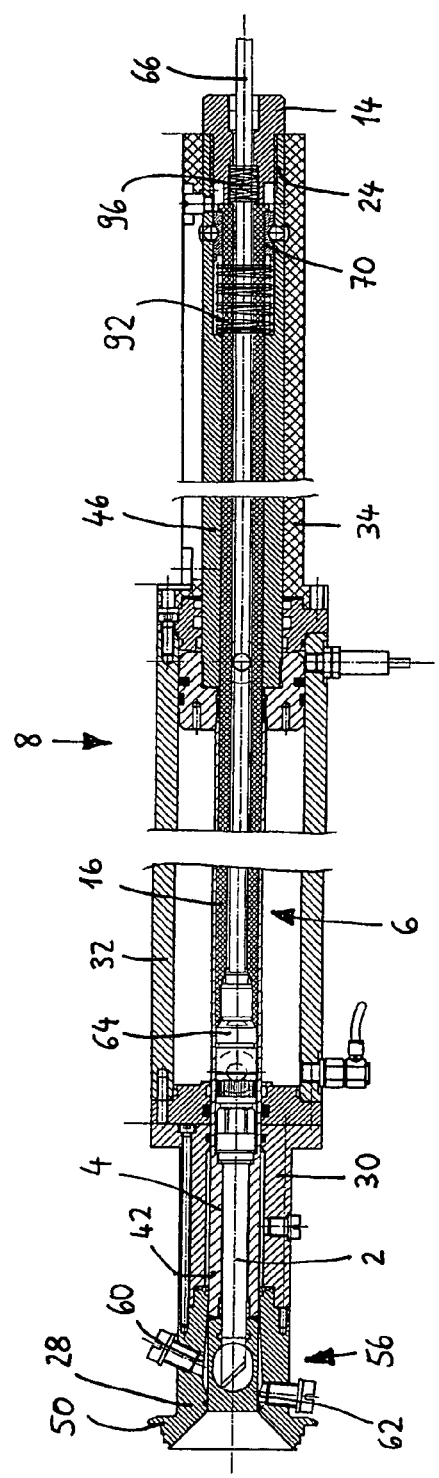
Fig. 2
Fig. 1

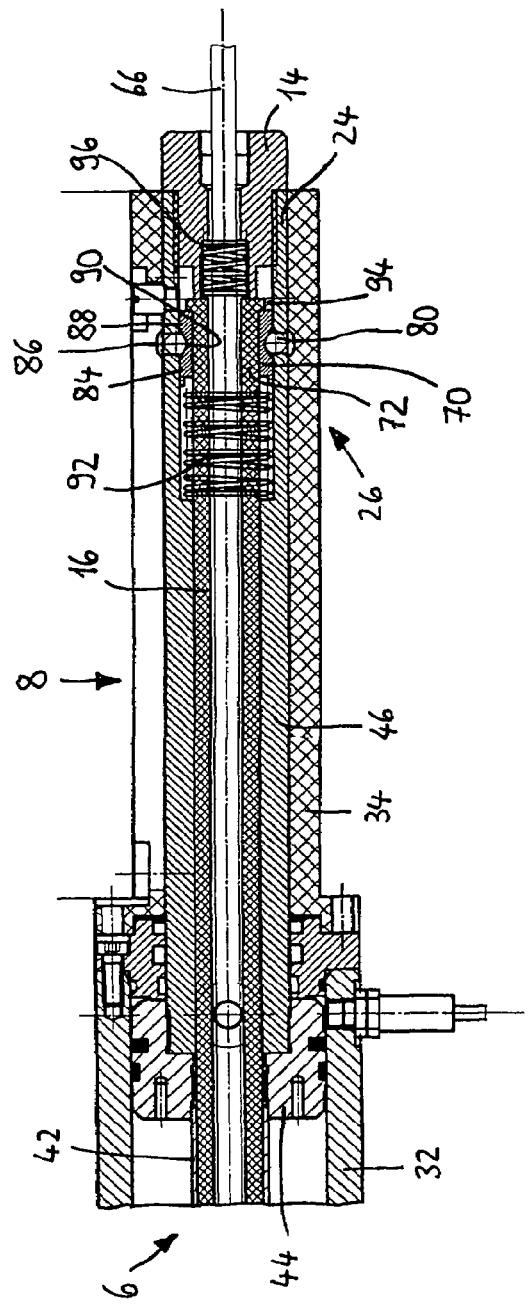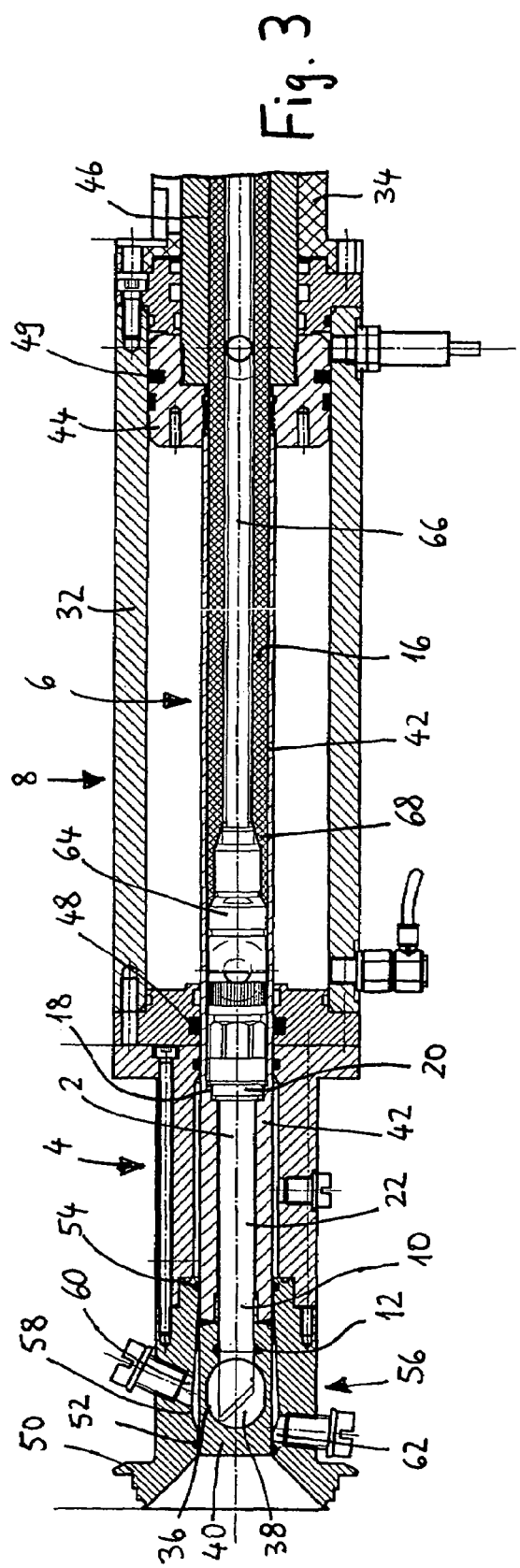

US 7,272,983 B2

PROBE-HOLDER ARMATURE WITH A SENSOR PROBE

TECHNICAL FIELD

The invention relates to a probe-holder armature with a sensor probe.

BACKGROUND OF THE INVENTION

A probe-holder armature of the kind mentioned above is known, for example from EP 0 882 896 A1, where a probe-holder armature is described with a sensor probe that is removably arranged in an immersion tube. The immersion tube is axially movable in a housing between a retracted rest position and a deployed working position in order to bring the anterior part of the sensor probe into contact with a measuring medium. The sensor probe in its installed condition provides a medium-tight closure of the immersion tube, for example by means of a ring seal that is arranged between the immersion tube and the sensor probe housing. If the immersion tube is deployed from the rest position into the working position when no sensor probe is installed, the absence of the medium-tight closure can have the undesirable consequence of allowing measuring medium to escape into the empty immersion tube and other parts of the probe-holder armature. The probe-holder armature according to the aforementioned reference is therefore equipped with a safety device which prevents axial movement of the immersion tube when no sensor probe is in place.

In the probe-holder armature according to EP 0 882 896 A1, an external screw thread in the rear portion of the sensor probe shaft serves to screw the sensor probe into a matching internal thread of the immersion tube. By turning the sensor probe into the immersion tube, a sleeve-like safety slide that is arranged coaxially inside the immersion tube is moved from a position where the immersion tube is locked against axial movement to a position where the immersion tube is free to move. As a consequence of this functional principle of the safety device, the immersion tube needs to have substantially the same length as the sensor probe. However, since the deployment depth of the immersion tube, i.e., the distance between the retracted rest position and the maximally deployed position of the immersion tube is of necessity shorter than the length of the immersion tube, the largest possible deployment depth is limited by the length of the sensor probe. Accordingly, with a probe-holder armature according to the aforementioned prior-art reference, a sensor probe of the very common length of 12 cm can be deployed to a maximum depth of slightly less than 12 cm. However, this is inadequate for many types of measurements, for example for measurements in large reaction vessels.

A probe-holder armature is described in EP 0 106 858 B1, where a sensor probe is arranged in an immersion tube that can be significantly longer than the sensor probe. In this case, the measuring tip of the sensor probe protrudes from the open front end of the immersion tube. The housing part that connects to a reaction vessel has at its front end a perforated cage into which the frontal part of the immersion tube—more specifically the sensor tip that protrudes from the immersion tube—is pushed in order to reach the deployed measuring position. A spring that is arranged in the cage applies a biasing force to the immersion tube towards the retracted rest position and thereby holds an anterior closure member of the immersion tube in a closed position, so that in order to deploy the immersion tube, it is necessary to first overcome the pre-tensioning force of the spring. While the deployment depth in this probe-holder armature is not limited by the sensor probe length, the deployment depth is nevertheless restricted by the displacement distance of the pre-tensioning spring, which in practice represents a considerable disadvantage. It also proves to be disadvantageous that the sensor probe or its holder serves as the means of opening the closure member when the sensor probe is deployed into the measuring position, in which case the front end of the sensor probe or its holder pushes the closure member open against the force of the pre-tensioning spring. Consequently, the front end of the sensor probe has to be particularly robust, or the holder has to be equipped with a pusher element at its front end. A pusher element of this kind represents one more component in the assembly and can furthermore interfere with the measuring function of the sensor probe. In addition, the spring in the cage is exposed to contamination by the measuring medium and difficult to clean. As a further aggravating disadvantage, the probe-holder armature according to EP 0 106 858 B1 has no protection whatsoever against being deployed when there is no sensor probe installed.

SUMMARY OF THE INVENTION

The task set for the invention is to propose an improved probe-holder armature to avoid in particular the aforementioned disadvantages.

This task is solved by the probe-holder armature as defined in claim 1, wherein a sensor probe is removably arranged in the front part of an immersion tube which is axially movable in a housing between a retracted rest position and a deployed working position and wherein the sensor probe in its installed condition provides a medium-tight closure of the immersion tube.

The position-related terms "front", "forward", "anterior" or variations of these terms refer to elements which in the operating state of the probe-holder armature are facing towards, or are positioned closer to, a reaction vessel to which the probe-holder armature is connected. Analogously, the position-related terms "back", "rear", "rearward" or variations of these terms refer to elements which are facing away, or are positioned farther away, from the reaction vessel.

Due to the feature that the immersion tube has a removable insert which can be held in a fixed position by means of a closure member and which allows the sensor probe in its installed position to be pushed forward against an anterior stop of the immersion tube, the overall length of the immersion tube and thus the deployment depth between the retracted rest position and the deployed working position can be dimensioned significantly longer than the length of the sensor probe.

There is a safety device which has a safety slide that surrounds the rear end of the insert like a sleeve and which is movable between a further forward stop and a rearward stop inside the immersion tube from a first locking position through a releasing position to a second locking position, wherein the safety slide cooperates with at least one locking member that is arranged with radial mobility in the immersion tube. In the locking position of the safety slide, the locking member sits with its inward-facing side against the outside surface of the safety slide while the outward-facing side of the locking member engages a locking recess in the housing. In the releasing position of the safety slide, the locking member engages at its inward-facing side a circumferential groove in the safety slide, while the outward facing side of the locking member is freed from the locking recess of the housing. This prevents an axial movement of the immersion tube out of its rest position if one or more of the three components sensor probe, insert and closure member are missing, whereby an all-encompassing degree of operating safety is achieved against an inadvertent manipulation of the probe-holder armature while a component is missing. Particularly in a probe-holder armature that is connected to a reaction vessel or to a similar piece of equipment, it is possible to prevent the immersion tube from being moved inadvertently and causing harm in a case where a component is not installed, for example because of maintenance or replacement.

Advantageous further developed embodiments of the invention are defined in the dependent claims.

In principle, the insert can have different shapes; it could for example be shaped as a rod. According to claim 2, the insert is configured in a tubular shape and has in addition a front side that sits against a matching rearward-facing side of the sensor probe, preferably against the sensor probe shaft. A compact design configuration of the probe-holder armature is defined in claim 3, according to which the closure member can be inserted at the rear end of the immersion tube and, in its inserted condition, keeps the insert seated against the sensor probe and the latter against the forward stop.

The probe-holder armature according to claim 4 is particularly preferred in regard to the design configuration of the safety device.

According to claim 4, the safety slide has a forward locking area, a rearward locking area, as well as a circumferential groove around its middle and is pre-tensioned against the rear end of the immersion tube by means of a first spring, and—if the insert is in place—sits against a rearward flange of the insert. Arranged on the closure member is a second spring by means of which the insert is pre-tensioned against the front end of the immersion tube, with the entire arrangement working in such a way that:
  a. when the closure member is missing, the forward locking area of the safety slide is located opposite the locking member;
  b. when the insert is missing, the forward locking area of the safety slide is located opposite the locking member;
  c. when the closure member is in place and the sensor probe is missing, the rearward locking area of the safety slide is located opposite the locking member;
  d. in the operative state, the circumferential groove in the middle of the safety slide is located opposite the locking member.

The fact that, according to claim 5, the insert, the second spring and the closure member are each equipped with a lateral passage opening facilitates the installation and removal of the sensor probe. This feature is particularly suitable for sensor probes that have a cable with a comparatively bulky connector plug so that it cannot be threaded into the tubular insert.

According to claim 6, an anterior part of the housing includes a rinsing area with an inlet and a drainage outlet for a rinsing medium. The term "rinsing medium" in the present context includes not only an actual rinsing liquid such as for example water, but also encompasses cleaning media of the type used in the so-called CIP (cleaning in place) method, or for example calibration fluids, rinsing gas and the like. According to claim 7, it is advantageous if the rinsing area is delimited by a forward ring seal and a rearward ring seal which together with the associated parts of the cylindrical outside surface of the immersion tube form medium-tight closure barriers. A space-saving configuration is obtained in accordance with claim 8, according to which the immersion tube is closed off at the front end and has at least one lateral opening which, in a rinsing position of the immersion tube, lies between the forward and rearward ring seals. With this arrangement, the sensor probe is protected from mechanical damage also when the immersion tube is in the deployed position, since the sensor probe does not protrude from the end of the immersion tube. According to claim 9, the rinsing position of the immersion tube is preferably identical with the retracted rest position.

In the embodiment according to claim 10, the immersion tube has a section configured as a piston which is held in a cylindrical section of the housing with axial mobility between the retracted rest position and the deployed working position. By using appropriate glide bushings, a guided gliding motion in the lengthwise direction with low friction is assured, which has the particular benefit of avoiding a mechanical stress on the ring seals that are arranged between the housing and the immersion tube.

In principle, the probe-holder armature can be designed for manual operation. However, according to claim 11, the probe-holder armature is provided with a fluid-operated actuator device using, e.g., compressed air or hydraulic oil to drive the axial movement of the immersion tube.

BRIEF DESCRIPTION OF THE DRAWINGS

Embodiments of the invention will be described below with references to the drawings, wherein:

FIG. 1 represents a lengthwise sectional view of a probe-holder armature with the immersion tube shown in the retracted rest position;

FIG. 2 represents a lengthwise sectional view of the probe-holder armature of FIG. 1 with the immersion tube shown in the deployed working position;

FIG. 3 represents the anterior part of the probe-holder armature of FIG. 1 in an enlarged view;

FIG. 4 represents the rear part of the probe-holder armature of FIG. 1 in an enlarged view;

DETAILED DESCRIPTION OF PREFERRED EMBODIMENT(S)

Figure 5:
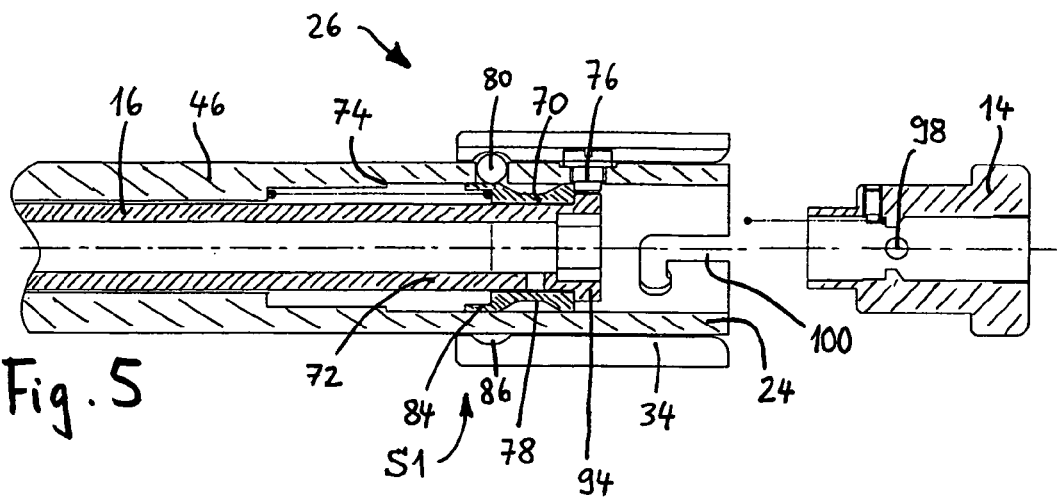
FIG. 5 represents a lengthwise sectional view of the rear end portion of a probe-holder armature with the closure member missing.

The probe-holder armature illustrated in the FIGS. 1 to 4 contains a sensor probe 2 which is arranged as a removable device in the forward portion 4 of an immersion tube 6. The immersion tube 6, and along with it the sensor 2, are axially moveable relative to a housing 8 between a retracted rest position and a deployed working position. In the rest position, which is shown in FIG. 1, the immersion tube 6 and the sensor probe 2 are inside the housing 8. In the working position as shown in FIG. 2, the immersion tube 6 with the sensor probe 2 is deployed and immersed in a reaction vessel (not shown) to perform measurements in a medium contained in the reaction vessel.

An anterior wall section 10 of the sensor probe 2 and an O-ring 12 imbedded in the forward portion 4 of the immersion tube 6 form a medium-tight closure of the immersion tube 6. The immersion tube 6 further contains a removable tubular insert 16 which can be locked in place by means of a closure member 14. By means or the tubular insert 16, the sensor probe 2 in its installed position is pushed against a forward stop 18 of the immersion tube 6. The forward stop 18 in the illustrated example is formed by a narrowing step of the interior diameter of the immersion tube 6 against which the sensor 2 seats itself with a projection 20 of the sensor shaft 22.

As can be seen in FIGS. 1, 2 and 4, and also according to the following detail explanation, the closure member 14 can be inserted at the rear end 24 of the immersion tube 6. In its installed condition, the closure member 14 keeps the insert seated against the sensor probe 2 and the latter against the forward stop 18.

The probe-holder armature is further equipped with a safety device 26 which prevents the immersion tube 6 from moving out of the rest position if one or more of the three components sensor probe 2, insert 16 and closure member 14 are missing.

The housing 8 is composed of several tubular components, i.e., an anterior chamber part 28, an intermediate chamber part 30, a cylindrical housing part 32, as well as a rearward housing part 34. The individual chamber parts are connected to each other by connecting flanges and fastening screws.

At its front end, the immersion tube 6 has a cage 36 with at least one lateral opening 38 which in the deployed working condition allows the measuring medium to reach the sensor probe 2. The cage 36 further has a floor 40 which closes off the front end of the immersion tube. The cage 36 is welded to an intermediate part 42 of the immersion tube. The aforementioned forward stop 18 for the sensor 2 is formed on the inside wall of the intermediate part 42 of the immersion tube. At its opposite end from the cage 36, the intermediate part 42 of the immersion tube is connected to a piston 44 which is supported with axial mobility inside the cylindrical housing part 32. A rearward part 46 of the immersion tube is arranged on the side of the piston 44 that faces away from the intermediate part 42. The rear end 24 of the rearward part 46 of the immersion tube is equipped with a seat for the closure member 14. As can be seen in particular in FIG. 3, a plurality of slide bushings 48 are provided between the cooperating parts of the housing 8 and the immersion tube 6.

The anterior chamber part 28 is equipped with a connector flange 50, by means of which the probe-holder armature can be connected to a reaction vessel. Since the anterior chamber part 28 is configured as a component of the modular assembly of the housing 8, the probe-holder armature can be attached to reaction vessels with differently dimensioned connecting arrangements by using an anterior chamber part 28 with an appropriately sized connecting flange 50.

As can likewise be seen in FIG. 3, the anterior chamber part 28 is configured as a part of a rinsing device for the sensor 2. To perform this function, the anterior chamber part 28 includes a rinsing area 56 delimited by an anterior ring groove 52 and a rearward ring groove 54, with a circumferential wall 58 having an inlet 60 as well as a drainage outlet 62 for a rinsing medium. Each of the ring grooves 52, 54 holds a seal ring in tight contact with the exterior wall of the immersion tube 6 to form a medium-tight seal of the rinsing area 56. When the immersion tube 6 is in the retracted rest position which also represents a rinsing position for the sensor probe 2, the cage 36 is located within the rinsing area 56. Consequently, rinsing medium supplied through the inlet 60 can enter through the lateral passage opening 38 of the cage 36 to reach the sensor probe 2 inside the cage 36. An escape of rinsing medium into the probe-holder armature is prevented by an O-ring 12 that is arranged between the outside wall 10 of the sensor probe 2 and the inside wall of the immersion tube 6. In the deployed measuring position, a part of the immersion tube 6 with no openings is positioned in the anterior chamber part 28, so that the rinsing area 56 is limited to the enclosed space from the ring groove 52 to the ring groove 54 between the outside wall of the immersion tube 6 and the circumferential wall 58.

As a practical matter, the inlet 60 and the outlet 62 are provided with internal screw threads to receive either a corresponding mating part or, as shown in FIGS. 1 and 2, a closure plug. The latter is useful in particular for performing leak tests.

The term "rinsing medium" in the present context includes not only an actual rinsing liquid such as water. Depending on the application, this term also encompasses a variety of cleaning media, e.g., of the type used in the so-called CIP (cleaning in place) method. Other possible media include steam, rinsing gases, or also calibration fluids. In particular, the inlet 60 or in some cases also the outlet 62 can be connected to a sensor-treatment apparatus with the capability to perform an entire sequence of cleaning-, rinsing- and calibrating steps. Furthermore, there can be more than one inlet as well as more than one drainage outlet.

The sensor probe 2 has a plug header with electrical connections at the rear, which couples to a matching connector plug 64 with connecting cable 66. The connector plug 64 is stepped down towards the rear and is backed by an entrance opening 68 of the insert 16 that has a stepped profile of complementary shape. The connecting cable 66 runs inside the insert 16 to the rear end 24 of the immersion tube 6 and from there through the closure member 14 to the outside. As mentioned above, the insert 16 holds the sensor probe 2 against the forward stop 18 of the immersion tube 6. Thus, the sensor probe 2 and the insert 16 need to be matched to each other not only in their respective shapes but also with regard to their lengths, so that their combined length approximately matches the length of the immersion tube.

The safety device 26, which prevents the immersion tube 6 from moving axially out of its rest position when the sensor 2 or the insert 16 or the closure member 14 or more than one of these components is missing, is constructed in accordance with the following description.

As can be seen in particular in FIGS. 5 to 8, the rearward part 46 of the immersion tube contains a safety slide 70 which surrounds the rear end portion 72 of the tube-shaped insert 16 like a sleeve. The safety slide 70 is movable inside the rearward part 46 of the immersion tube between a forward and rearward stop from a first locking position S1 through a releasing position F into a second locking position S2. In the illustrated example, the forward stop is formed by a step-like constriction 74 in the interior of the rearward part 46 of the immersion tube, while the rearward stop is formed by a pin 76 that is screwed into or otherwise fastened to the wall of the rearward part 46 of the immersion tube. The outer side wall of the safety slide 70 is designed as a guide-profile surface 78 for a plurality of locking members 80. Each locking member 80 consists of a ball that is arranged with radial mobility in an associated passage bore in the rear part 46 of the immersion tube.

In the first locking position S1, the safety slide 70 sits against the rearward stop 76 while each locking member 80 sits at its inward-facing side against the forward locking portion 84 of the guide-profile surface 78 and is thereby caused to engage with its outward-facing side a locking recess 86 of the housing 8. The locking recess 86 is configured as a ring groove in the inward-facing wall of the rearward housing part 34. This engagement blocks the axial mobility of the immersion tube 6 in relation to the housing 8. In the second locking position S2, the safety slide 70 sits against the forward stop 74 while each locking member 80 sits at its inward-facing side against the rearward locking portion 88 of the guide-profile surface 78 and is thereby again caused to engage with its outward-facing side the locking recess 86 of the housing 8. As in the first locking position S1, the axial mobility of the immersion tube 6 in relation to the housing 8 is blocked. In the released position F, the safety slide 70 is located in the area between the two stops 74 and 76, so that each locking member 80 recedes on the inside into a circumferential groove in the middle of the guide-profile surface 78 while the outward side of the locking member is freed from the locking recess 86 of the housing with the result that the axial mobility of the immersion tube 6 in relation to the housing 8 is released.

Figure 6:
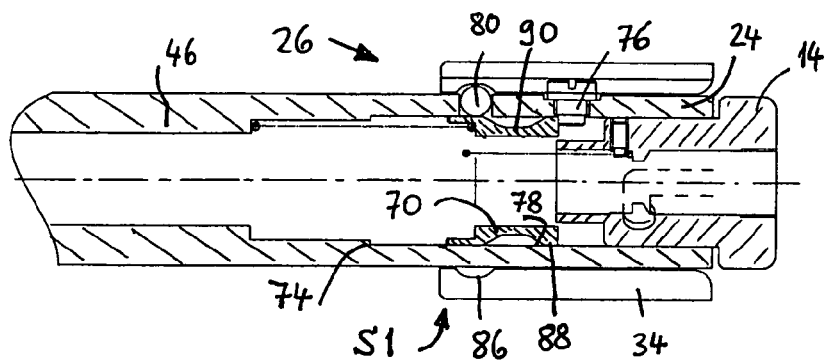
FIG. 6 represents a lengthwise sectional view of the rear end portion of FIG. 5 with the insert missing.
Figure 7:
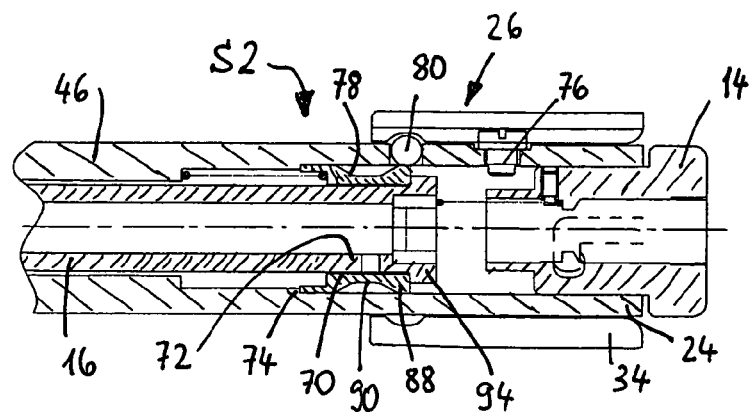
FIG. 7 represents a lengthwise sectional view of the rear end portion of FIG. 5 with the closure member in place and the sensor probe missing.
Figure 8:
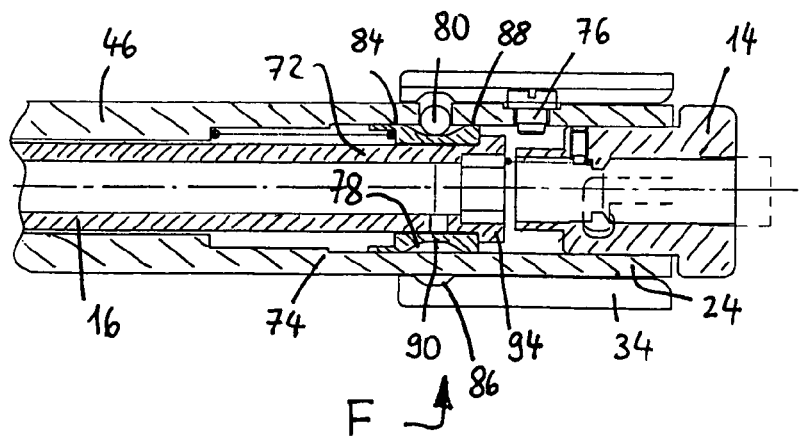
FIG. 8 represents a lengthwise sectional view of the rear end portion of FIG. 5 in the operative state of the probe-holder armature.

As can be seen in particular in FIG. 4, the safety slide 70 is pre-tensioned against the rear end 24 of the immersion tube 6 by means of a first spring 92 and, if the insert 16 is in place, the safety slide 70 sits against a rearward flange 94 of the insert 16. Arranged on the closure member 14 is a second spring 96 by means of which the insert 16 and thus also the safety slide 70 is pre-tensioned against the front end of the immersion tube 6. As a result, the safety device performs its function as follows:

if the closure member 14 is missing, the second spring 96 is likewise missing. As a result, the safety slide 70 is pushed by the first spring 92 against the rearward stop 76, i.e., the safety slide 70 is held in the first locking position S1 where the forward locking portion 84 is positioned opposite the locking members 80 (FIG. 5). This occurs regardless of the presence of the sensor probe 2 and/or the insert 16.

if the insert 16 is missing—and regardless of whether the sensor probe 2 is installed or not—, the safety slide 70 is pushed by the first spring 92 against the rearward stop 76, i.e., the safety slide 70 is held in the first locking position S1 where the forward locking portion 84 is positioned opposite the locking members 80 (FIG. 6). Although the second spring 96 is in place, it remains ineffective because of the missing insert 16;

when the closure member 24 is in place and the sensor probe 2 is missing, the second spring 96 pushes the insert 16—and with it the safety slide 70 which is taken along by the rearward flange 94—against the forward stop 74 and thus holds the insert 16 and safety slide 70 in the second locking position S2, where the rearward locking portion 88 is positioned opposite the locking members 80 (FIG. 7). Here, the essential point is that the force of the second spring 96 has to exceed the opposing force of the first spring 92. Because of the missing sensor probe 2, the forward stop 18 of the immersion tube 6 remains ineffective.

in the operative state, i.e., if the sensor probe 2, the insert 16 and the closure member 14 are all in place, the play of forces per se is the same as described above under c). The insert 16 and thus the safety slide which is taken along by the rearward flange 94 are again pushed forward. However, the first locking position S1 is not attained, because the sensor probe 2 sits against the forward stop 18 in the immersion tube 6 and thus prevents the insert 16 from being pushed farther forward. As a result, the safety slide 70 is held in the releasing position F where the circumferential groove 90 in the middle of the guide-profile surface 78 is located opposite the locking members 80.

As can be concluded further from the preceding discussion, the safety device 26 is responsive not only to the absence of components but also to components that are installed incorrectly or are of the wrong dimensions. This will be explained in more detail below.

In the case where the sensor probe is too short, the forward stop 18 is ineffective, i.e., the safety slide 70 ends up in the first locking position S1. On the other hand, if the sensor probe is too long, the insert cannot be pushed forward enough to reach the releasing position F, so that the safety slide 70 remains in the second locking position S2. An analogous conclusion can be made for the case where the insert 16 is either too short or too long.

As can be concluded from FIGS. 5 to 8, the rearward closure member 14 is equipped with a laterally projecting peg 98 which engages an L-shaped entry guide slot 100 at the rear end 24 of the immersion tube 6. By inserting and then turning the closure member 14, the latter is brought into a position that is locked against movement in the lengthwise direction. If the closure member 14 is installed without locking, it will be pushed out of the insertion tube 6 by the first spring 92, which causes the safety slide 70 to be moved to the first locking position S1.

In an embodiment that is not shown in detail, the tubular insert 16, the second spring 96 and the closure member 14 are each equipped with a lateral opening extending over their entire respective lengths. In the second spring 96, this opening is achieved with an arrangement in which the windings do not run in complete circles, which is known per se, while the opening in the insert 16 and in the closure member 14 is configured as a lateral slot. As the connecting cable 66 can be laid into the slotted component from the side without a threading-in procedure, it is possible, e.g., to also install sensor probes with bulky connector plugs, attached preamplifiers and the like in the probe holder armature.

It is practical to equip the probe holder armature with a lock against rotation to prevent turning of the immersion tube about its longitudinal axis. This is accomplished, e.g., by providing the rearward part 46 of the immersion tube with a projection that engages a matching lengthwise slot of the rear portion 34 of the housing. This ensures on the one hand that the passage openings 38 in the cage 36 are in a defined alignment relative to the inlets and outlets of the rinsing area 56. On the other hand, the rotation lock ensures that for sensor probes that are not rotationally symmetric the sensitive surface will be positioned in a desired alignment, for example in relation to a flow direction in the reaction vessel.

The lengthwise movement of the piston 44 in the cylindrical housing part 32 can be actuated manually or by means of a suitable pressure-driven device which is operated for example with compressed air, hydraulic oil, water, or another suitable fluid. As a further practical feature, there are position feedback devices through which the longitudinal position of the immersion tube can be determined.

In the deployed working position, which is shown in FIG. 2, the rear end 24 of the immersion tube 6 as well as the closure member 14 that is installed in the immersion tube are positioned in the rearward housing part 34, so that the closure member 14 is not immediately accessible. An inadvertent removal of the closure member 14 in the deployed working position is thus prevented. Particularly in the case of a pressurized reaction vessel, this represents an additional safeguard against an unwanted escape of reaction medium.

Although the probe-holder armature has been shown in horizontally installed positions, it can in principle also be installed vertically with the sensor probe directed downwards, or with an orientation in between the horizontal and vertical.

LIST OF REFERENCE SYMBOLS 2 sensor probe
4 forward portion of 6
6 immersion tube
8 housing
10 anterior wall section of 2
12 O-ring
14 closure member
16 insert
18 forward stop of 6
20 projection of 22
22 sensor probe shaft
24 rear end of 6
26 safety device
28 anterior chamber part of 8
30 intermediate chamber part
32 cylindrical housing part
34 rearward part of housing
36 cage of 6
38 passage opening of 36
40 floor of 36
42 intermediate part of immersion tube
44 piston
46 rearward part of immersion tube
48 slide busing
50 connecting flange of 28
52 anterior ring groove
54 rearward ring groove
56 rinsing area
58 circumferential wall of 56
60 inlet
62 drainage outlet
64 connector plug
66 connecting cable
68 anterior entrance opening of 16
70 safety slide
72 rear end portion
74 forward stop
76 rearward stop
78 outside wall (guide profile surface) of 70
80 locking member
84 forward locking portion of 78
86 locking recess
88 rearward locking portion of 78
90 circumferential groove around the middle of 78
92 first spring
94 rearward flange of 16
96 second spring
98 laterally projecting peg of 14
100 entry guide slot for 98

The invention claimed is:

1. Probe-holder armature comprising:
a sensor probe that is removably arranged in the forward portion of an immersion tube with a cylindrical outside surface, the immersion tube being axially movable in a housing between a retracted rest position and a deployed working position,
wherein the sensor probe in its installed condition provides a medium-tight closure of the immersion tube,
wherein the immersion tube has a removable insert which can be held in a fixed position by means of a closure member and by means of which the sensor probe in its installed position is pushed forward against a forward stop of the immersion tube,
wherein a safety device is provided which prevents an axial movement of the immersion tube out of its rest position if one or more of the three components including sensor probe, insert and closure member are missing,
characterized in that the safety device has a safety slide which surrounds the rear end of the insert and which is slidingly movable between a further forward stop and a rearward stop inside the immersion tube from a first locking position through a releasing position to a second locking position, wherein the safety slide cooperates with at least one locking member that is arranged with radial mobility in the immersion tube, wherein in each locking position of the safety slide, each said locking member sits with its inward-facing side against the outside surface of the safety slide while the outward-facing side of each said locking member engages a locking recess in the housing, and wherein in the releasing position of the safety slide each said locking member engages at its inward-facing side a circumferential groove in the safety slide, while the outward-facing side of each said locking member is freed from the locking recess of the housing.

2. Probe-holder armature according to claim 1, characterized in that the insert is configured in a tubular shape and has a front side that sits against a matching rearward-facing side of the sensor probe.

3. Probe-holder armature according to claim 1 or 2, characterized in that the closure member can be inserted at the rear end of the immersion tube and, in its installed condition, keeps the insert seated against the sensor probe and also keeps the latter seated against the forward stop.

4. Probe-holder armature according to claim 1, characterized in that the safety slide has a forward locking portion, a rearward locking portion as well as a circumferential groove around its middle, and that the safety slide is pre-tensioned against the rear end of the immersion tube by means of a first spring and that when the insert is in place, the safety slide sits against a rearward flange of the insert, wherein by means of a second spring that is arranged on the closure member, the insert is pre-tensioned against the front end of the immersion tube, with the entire arrangement working in such a way that:
a) when the closure member is missing, the safety slide is in position with the forward locking portion located opposite each said locking member;
b) when the insert is missing, the safety slide is in position with the forward locking portion located opposite each said locking member;
c) when the closure member is in place and the sensor probe is missing, the safety slide is in position with the rearward locking portion located opposite each said locking member; and:
d) in the operative state, the safety slide is in position with the circumferential groove in the middle of the safety slide located opposite each said locking member.

5. Probe-holder armature according to claim 4, characterized in that the insert, the second spring and the closure member are each equipped with a lateral opening extending over their entire respective lengths.

6. Probe-holder armature according to claims 1, 2, 4, or 5, characterized in that an anterior part of the housing includes a rinsing area with at least one inlet and a drainage outlet for a rinsing medium.

7. Probe-holder armature according to claim 6, characterized in that the rinsing area is delimited in front and back by ring seals which form medium-tight closure barriers together with the associated parts of the cylindrical outside surface of the immersion tube.

8. Probe-holder armature according to claim 7, characterized in that the immersion tube is closed off at the front end and has at least one lateral opening which, in a rinsing position of the immersion tube, lies between the forward and rearward ring seals.

9. Probe-holder armature according to claim 8, characterized in that the rinsing position of the immersion tube is identical with the retracted rest position.

10. Probe-holder armature according to claim 1, characterized in that the immersion tube has a section configured as a piston which is held in a cylindrical section of the housing with axial mobility between the retracted rest position and the deployed working position.

11. Probe-holder armature according to claim 10, characterized in that the probe-holder armature comprises a fluid-operated actuator device to drive the axial movement of the immersion tube.

* * * * *